United States Patent [19]

Inoue et al.

[11] Patent Number: 4,675,339

[45] Date of Patent: Jun. 23, 1987

[54] SPHERICAL AMINO ACID PREPARATION

[75] Inventors: Yoshimi Inoue, Takasaki; Mamoru Seki, Fujioka; Mamoru Katagiri, Kamisato; Hiroaki Nishiyama, Tamamura; Zenji Ogawa, Takasaki, all of Japan

[73] Assignee: Nippon Kayaku Kabushiki Kaisha, Tokyo, Japan

[21] Appl. No.: 728,504

[22] Filed: Apr. 29, 1985

[30] Foreign Application Priority Data

May 10, 1985 [JP] Japan ................................. 59-91826

[51] Int. Cl.$^4$ ................. A61K 31/195; A61K 31/405
[52] U.S. Cl. .................................... 514/419; 514/561; 514/567; 562/553; 562/554; 562/445; 424/35
[58] Field of Search ................ 548/497; 514/419, 561; 424/35, 319; 562/553, 554, 445

[56] References Cited

U.S. PATENT DOCUMENTS

| 3,657,144 | 4/1972 | Yoshida | 425/35 |
| 3,786,123 | 1/1974 | Katzen | 424/35 |
| 4,352,883 | 10/1982 | Lim | 424/35 |

FOREIGN PATENT DOCUMENTS

| 9055819 | 10/1972 | Japan | 514/719 |
| 0104010 | 6/1985 | Japan | 514/419 |

Primary Examiner—Richard L. Raymond
Assistant Examiner—D. B. Springer
Attorney, Agent, or Firm—Henry C. Nields

[57] ABSTRACT

The present invention relates to a spherical amino acid having an average particle size of about 1 mm or below and a process for the preparation thereof.

3 Claims, No Drawings

SPHERICAL AMINO ACID PREPARATION

BACKGROUND OF THE INVENTION

An amino acid, particularly L-amino acid is generally crystallized, for example, by adding a large amount of a lower alcohol such as methanol or ethanol to an aqueous solution thereof, if necessary followed by concentrating and cooling the mixture, to thereby crystallize the L-amino acid. According to such a process, a finely powdered crystalline amino acid is obtained. This fine crystalline amino acid has disadvantages in that the specific volume is generally about 5.2 ml/g, thus resulting in bulkiness and that it tends to be scattered in handling, for example, in packing a capsule.

Further, with regard to the process for the preparation, among the above processes, a process which comprises adding a lower alcohol to thereby crystallize an amino acid requires the recovery of the alcohol and is attended with the loss of the alcohol, thus resulting in economical disadvantages. Furthermore, according to a process which comprises crystallizing an amino acid by neutralization, too much fine crystal will be precipitated to stir the mixture sufficiently, if insufficient attention is paid to the concentration of an L-amino acid before neutralization, the addition rate of a base or an acid and the stirring speed. According to a process which comprises crystallizing an amino acid by concentration and cooling, the growth rate of crystal is varied depending upon the rate of the concentration and the cooling, so that it is difficult to obtain a uniform crystal. Additionally, according to a process which comprises concentrating under a reduced pressure with cooling, the precipitated L-amino acid is a fine crystal, so that it forms foam and eventually flows out of a concentrator, resulting in an impossibility of concentration.

SUMMARY OF THE INVENTION

The present invention relates to a composition comprising granules having an average particle size of about 1 mm or below comprising an amino acid and a polymer and a process for the preparation thereof.

It is an object of the present invention to provide an amino acid in granule form which has a high purity and can be easily handled with no scatter of powder. Additionally, it is another object of the present invention to obtain, without the step of an ordinary granulation, granules including an amino acid and having capsule-packing characteristics and tablet-formability which are equivalent to those of a granular amino acid prepared by prior-art granulation methods.

DETAILED DESCRIPTION OF THE INVENTION

A novel composition of the present invention can be prepared by the following procedure. That is to say, it can be obtained by crystallizing an amino acid from an aqueous solution thereof in the presence of one or more of polymers selected from the group consisting of water-soluble cellulose derivatives, water- or polar organic solvent-soluble polyvinyl compounds, water-soluble starch derivatives, gelatin and polypeptides comprising its partial hydrolyzate, alginates and polyacrylates.

The granules in the composition according to the present invention have an average particle size of about 1 mm or below, generally 0.1 to 1 mm, in many cases 0.2 to 1 mm, preferably 0.2 to 0.8 mm and a specific volume of about 1.2 to 4.0 ml/g, generally about 1.5 to 3.0 ml/g, in many cases 1.7 to 2.8 ml/g, which is remarkably decreased as compared with that of a powdered amino acid of the prior art, so that it exhibits an improved fluidity and can be easily handled as compared with a powdered amino acid of the prior art.

In the present invention, the average particle size was decided as follows:

The particles of the present invention are sieved to obtain on each particle having a definite particle size and the amount by weight of the each particle obtained is measured. Thereafter, an arithmetic mean is calculated.

Further, the amino acid of the present invention has a high purity of 95 to 99.6% (by weight: hereinbelow the same applies, unless otherwise stated) and contains at most 5% of polymers selected from the group consisting of water-soluble cellulose derivatives, water- or polar organic solvent-soluble polyvinyl compounds, water-soluble starch derivatives, gelatin and polypeptide comprising its partial hydrolyzate, alginates and polyacrylates.

Examples of the amino acid to be used in the present invention include leucine, isoleucine, valine, tryptophan, tyrosine and phenylalanine.

The aqueous solution of an amino acid to be treated by the process of the present invention is not particularly limited and may be any one prepared by fermentation, enzymatic, synthetic or other processes. The process of the present invention is generally applied to the crystallization of an L-amino acid, but may also be applied to the crystallization of a D-amino acid.

The process of the present invention can be carried out as follows: A base or acid is added to an aqueous solution of an acid or alkali salt of an amino acid containing the above additive to thereby neutralize the base or the acid and simultaneously crystallize the amino acid. Alternatively, an aqueous solution of an amino acid is concentrated under a reduced pressure and cooling in the presence of the above additive to thereby crystallize the amino acid. Additionally, in some cases, an aqueous solution of an amino acid containing the above additive is only cooled to thereby crystallize the amino acid.

The amount of the additive is 50 to 50,000 ppm, preferably 200 to 10,000 ppm, more preferably 1,000 to 6,000 ppm based on the amount of an amino acid.

The additive may be added as such to a solution of an amino acid. Alternatively, the additive can be added in a state dissolved or dispersed in a proper solvent.

The term "water-soluble" in the present invention, unless otherwise stated, involves the case where the pertinent substance is soluble in any of water, alkaline aqueous solution and acid aqueous solution. Examples of the above additive are as follows: Examples of the water-soluble cellulose derivative include methylcellulose, alkali metal salts of carboxymethylcellulose (for example, Na- or K-salt), hydroxypropylcellulose and hydroxypropylmethylcellulose phthalate, among which methylcellulose is the most preferred. Examples of the water- or polar organic solvent-soluble polyvinyl compounds include polyvinylpyrrolidone, polyvinyl alcohol and polyvinyl acetal diethylaminoacetate.

Examples of the water-soluble starch derivative include hydroxypropylstarch.

Examples of the gelatin and polypeptide comprising its partial hydrolyzate include alkali-treated gelatins, acid-treated gelatins and polypeptides comprising a partial hydrolyzate of gelatin having a molecular weight of several thousands to one hundred thousand.

Examples of the alginate include alkali metal alginates, for example, sodium alginate or potassium alginate.

Examples of the polyacrylate include polysodium acrylate.

Among these additives, ones which can attain only an anti-foaming effect are carboxymethylcellulose, water-soluble starch derivatives, gelatin, polypeptide comprising its partial hydrolyzate and the like, while others among the above additives not only exhibit an anti-foaming effect, but also are effective in precipitating a crystal not as a fine powder but as a spherical lump having an average particle size of 0.1 to 1 mm, in many cases 0.2 to 1 mm, most generally 0.3 to 0.8, thus facilitating efficient neutralization and concentration. The obtained crystal can be separated by an ordinary method such as centrifugation.

EFFECT OF THE INVENTION

According to the present invention, a foamy fine crystal disappears as a result of the presence of an additive and the precipitated crystal can be dispersed with simple stirring. Therefore, the neutralization proceeds efficiently in a process which comprises crystallizing by neutralization, and the decrease in the concentration rate and the flowing out of a concentrator are overcome in a process which comprises crystallizing by concentration, thus enabling a smooth concentration. As described above, the present invention enables a continuous crystallizing operation, thus establishing an industrially advantageous crystallizing method.

The spherical amino acid according to the present invention has a remarkably reduced specific volume as compared with that of the powdered amino acid of the prior art and exhibits an improved fluidity, resulting in very easy handling.

Accordingly, the spherical amino acid of the present invention exhibits, without an ordinary granulating step, capsule-packing characteristics and tablet-formability which are equivalent to those of ones prepared by granulating, so that it is suitable for such uses.

Now, the present invention will be illustrated by examples in more detail.

EXAMPLE 1

A fermentation liquor of L-isoleucine from which bacteria had been removed was passed through a cation exchange resin to adsorb the L-isoleucine. The adsorbed L-isoleucine was eluted with 1N-aqueous solution of caustic soda. The obtained eluate was concentrated to an L-isoleucine concentration of 150 g/l. 500 ml of the concentrated eluate was placed in a 1 l beaker and the additive as shown in Table 1 was added thereto. The mixture was neutralized with 35% hydrochloric acid to crystallize the L-isoleucine. The results are shown in Table 1.

TABLE 1

| Additive | Amount (ppm) | State of foam generation | State of crystal |
|---|---|---|---|
| none | — | foamy | fine powder |
| polyvinyl-pyrrolidone | 2000 | slightly foamy | small sphere |
| methyl-cellulose | 1000 | hardly foamy | small sphere |

EXAMPLE 2

500 ml of an aqueous solution of L-tryptophan (obtained by fermentation method) of a concentration of 40 g/l.H$_2$O and 90° C. was placed in a 1 l round-bottomed flask, followed by the addition of an additive as shown in Table 2. The mixture was cooled to 40° C., while stripping part of water by reducing a pressure with an evaporator, to crystallize the L-tryptophan. The results are shown in Table 2.

The obtained tryptophan had a purity of 98.4 to 98.6%. Further, with respect to spherical tryptophan, the average particle size was 0.4 to 0.6 mm and at least 90% of the particles have a size of 0.2 to 0.8 mm.

TABLE 2

| Additive | Amount (ppm) | State of foam generation | State of crystal |
|---|---|---|---|
| none | — | foamy | fine powder |
| carboxymethyl cellulose | 5000 | hardly foamy | " |
| methyl-cellulose | " | " | sphere |
| sodium salt of carboxy-methylcellulose | " | " | " |
| hydroxypropyl-cellulose | " | " | " |
| hydroxypropyl-methylcellulose phthalate | " | " | " |
| polyvinyl-pyrrolidone | " | " | " |
| polyvinyl alcohol | " | " | " |
| polyvinyl acetal diethyl-amino acetate | " | " | " |
| sodium alginate | " | " | " |
| hydroxypropyl-starch | " | " | fine powder |
| gelatin | " | " | " |
| poly sodium acrylate | " | " | sphere |

EXAMPLE 3

500 ml of an aqueous solution of L-tryptophan (obtained by fermentation method) of a concentration of 40 g/l.H$_2$O and 90° C. was placed in a 1 l round-bottomed flask, followed by the addition of an additive as shown in Table 3. The mixture was cooled to 40° C., while stripping part of water by reducing a pressure with an evaporator, to crystallize the L-tryptophan. The results are shown in Table 3.

The obtained spherical amino acid had a purity of 99.2 to 99.3% and an average particle size of 0.6 mm.

TABLE 3

| Additive | Amount (ppm) | State of foam generation | State of crystal | Concentration rate (ml/30 min) |
|---|---|---|---|---|
| none | — | foamy | fine powder | 125 |
| polyvinyl-pyrrolidone | 1000 | hardly foamy | sphere | 200 |
| methyl- | 750 | hardly | sphere | 200 |

TABLE 3-continued

| Additive | Amount (ppm) | State of foam generation | State of crystal | Concentration rate (ml/30 min) |
|---|---|---|---|---|
| cellulose | | foamy | | |

EXAMPLE 4

500 ml of an aqueous solution of L-phenylalanine (obtained by synthetic method) of a concentration of 80 g/l.$H_2O$ and 90° C. was placed in a 1 l round-bottomed flask. Polyvinylpyrrolidone and methylcellulose were added to the flask to give a concentration of 500 ppm each based on the L-phenylalanine. The mixture was cooled to 40° C., while reducing a pressure by stripping part of water with an evaporator, to crystallize the L-phenylalanine.

Foam was hardly generated and the concentration rate was 200 ml/30 min. The L-phenylalanine was precipitated in the form of small sphere.

We claim:

1. A process for preparing granules or powder having an average particle size of less than or equal to about 1 mm and comprising at least 95% by weight of an amino acid selected from the group consisting of leucine, isoleucine, valine, tryptophan, tyrosine or phenylalanine and at most 5% of at least one polymer selected from the group consisting of methylcellulose and hydroxypropylmethylcellulose phthalate, polyvinylpyrrolidone, polyvinylalcohol, polyvinyl acetal, diethylaminoacetate, hydroxypropyl starch, alkali-treated gelatins, acid-treated gelatins, a partial hydrolyzate of gelatin having a molecular weight of several thousands to one hundred thousand, alkali metal alginates and polyacrylates comprising adding the polymer or polymers to an aqueous solution containing the amino acid and thereafter neutralizing, cooling or concentrating the aqueous solution to the extent necessary to precipitate the said granules or powder from the aqueous solution containing the amino acid in the presence of one or more of said polymers.

2. A capsule containing granules or powder prepared according to the process of claim 1.

3. A tablet comprising granules or powder prepared according to the process of claim 1.

* * * * *